United States Patent [19]

Fontenot

[11] Patent Number: 5,423,321
[45] Date of Patent: Jun. 13, 1995

[54] DETECTION OF ANATOMIC PASSAGES USING INFRARED EMITTING CATHETER

[76] Inventor: Mark G. Fontenot, 229 Marilyn Dr., Lafayette, La. 70503

[21] Appl. No.: 190,516

[22] Filed: Feb. 2, 1994

Related U.S. Application Data

[63] Continuation-in-part of Ser. No. 16,565, Feb. 11, 1993, abandoned.

[51] Int. Cl.⁶ .............................................. A61B 5/00
[52] U.S. Cl. ...................................... 128/664; 128/899
[58] Field of Search ................... 128/664, 665, 899, 6, 128/7; 606/32, 34, 41

[56] References Cited

U.S. PATENT DOCUMENTS

| | | | |
|---|---|---|---|
| 4,898,175 | 2/1990 | Noguchi | 128/664 |
| 5,190,059 | 3/1993 | Fabian et al. | 128/899 |
| 5,211,165 | 5/1993 | Dumoulin et al. | 128/653.1 |

FOREIGN PATENT DOCUMENTS 2102127  1/1983  United Kingdom ............... 128/899

Primary Examiner—Ruth S. Smith
Attorney, Agent, or Firm—Howard L. Rose

[57] ABSTRACT

A method and apparatus is provided for reducing the danger of cutting into a passage or organ of the body during a surgical procedure by inserting a catheter into the passage or organ, the catheter having interiorly thereof an infrared radiator and employing an infrared detection system that produces a detectable signal indicative of the proximity of an infrared probe to the passage or organ the proximity of the probe to the passage or organ being a function of the approach of the surgical procedure to the passage or organ. The position of the infrared source and the probe may be reversed. Further a system for viewing the sight of the procedure and displaying the body into which the catheter is inserted is provided.

29 Claims, 10 Drawing Sheets

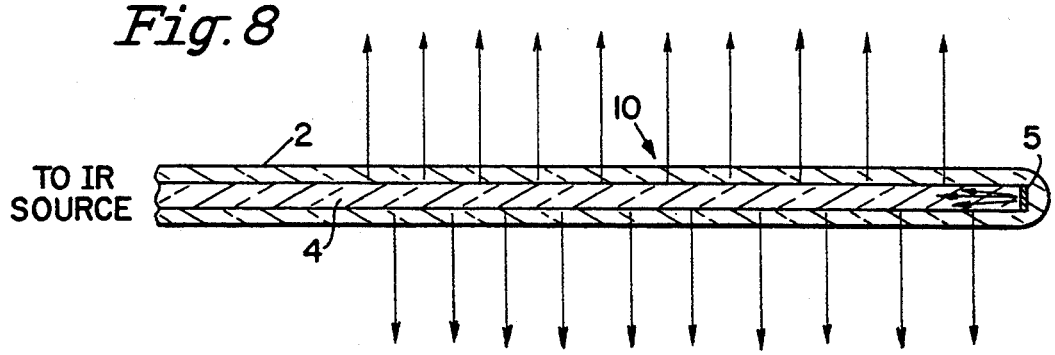
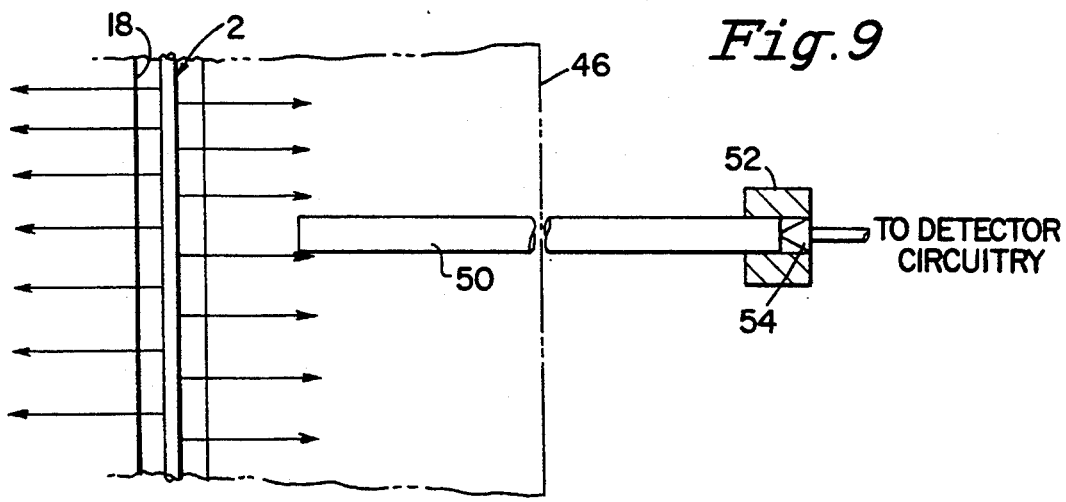
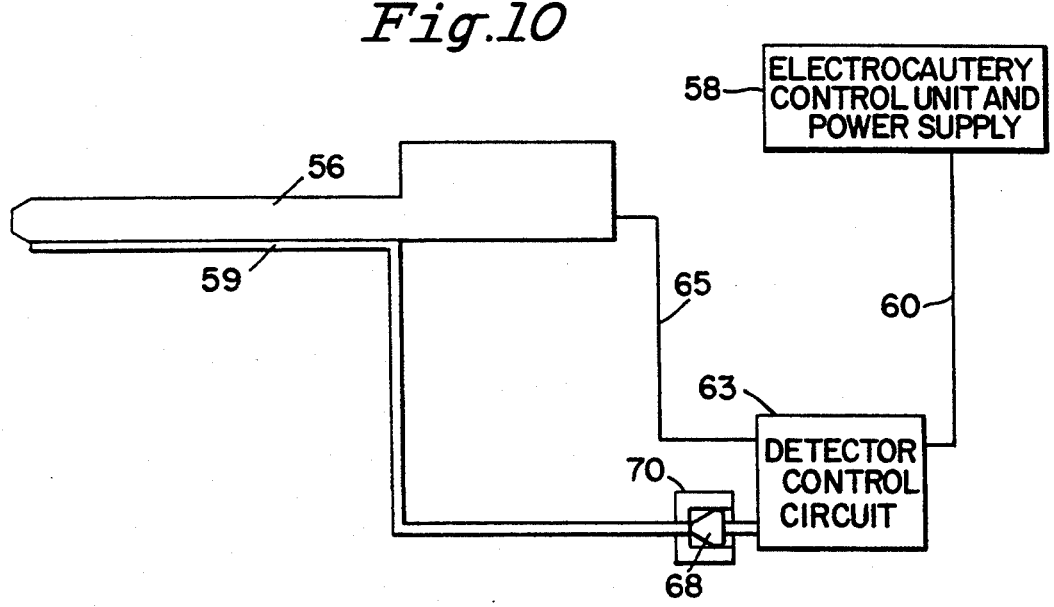

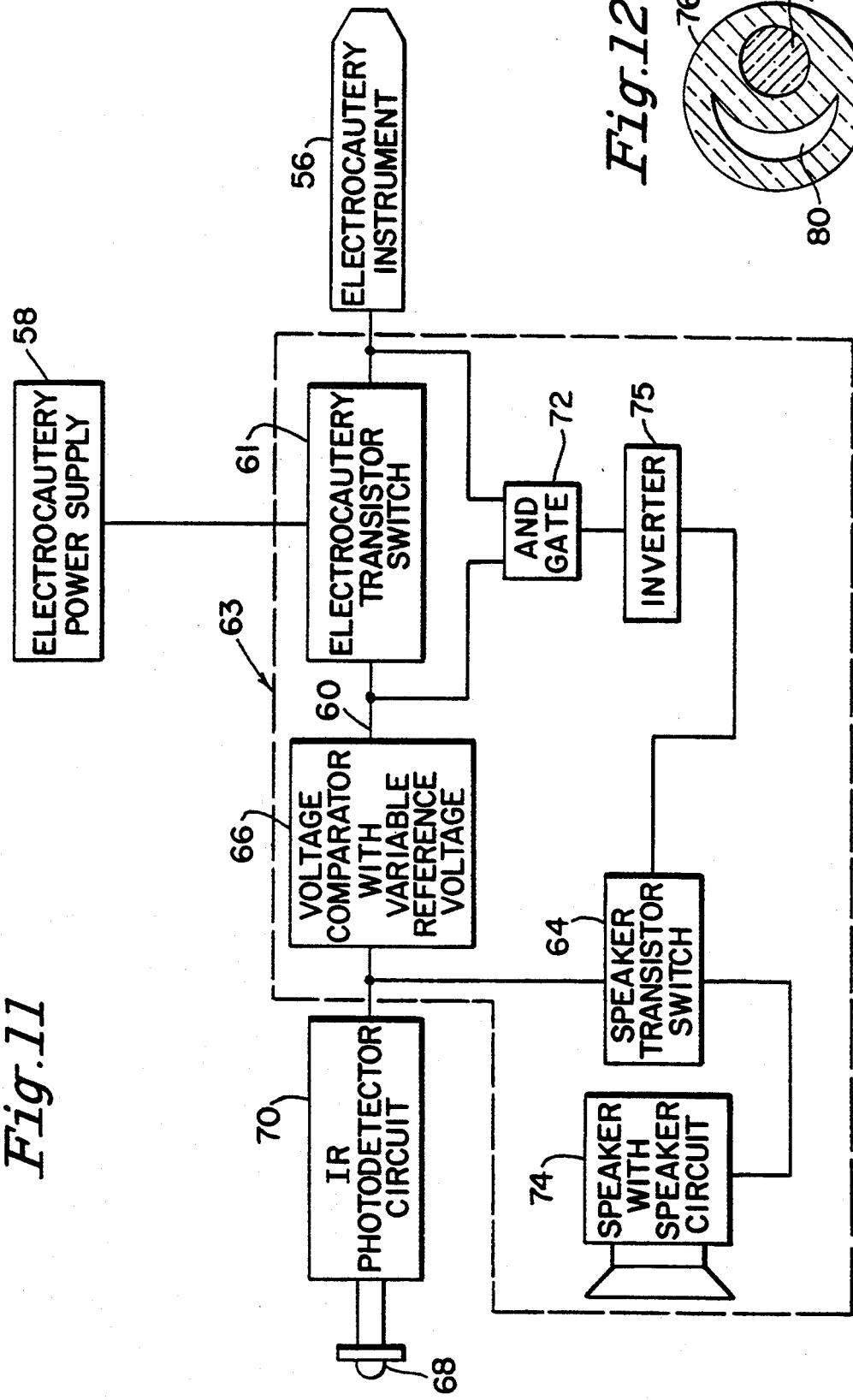
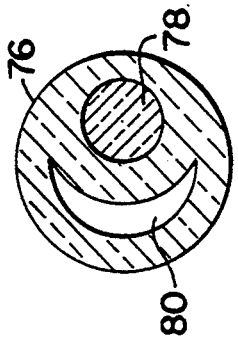

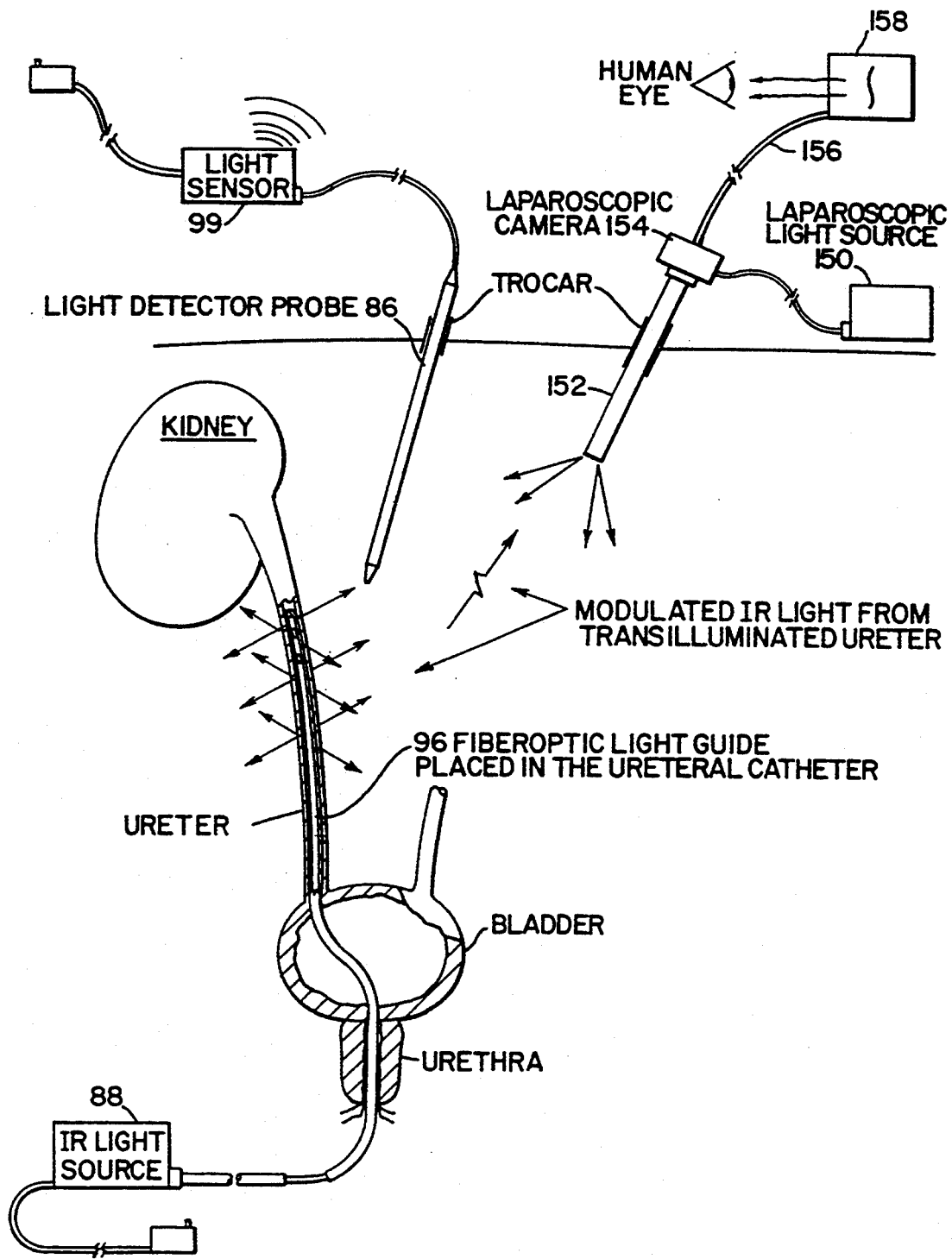

DETECTION OF ANATOMIC PASSAGES USING INFRARED EMITTING CATHETER

RELATED APPLICATIONS

This application is a continuation-in-part of Ser. No. 08/016,565, filed Feb. 11, 1993, now abandoned.

FIELD OF THE INVENTION

The present invention relates to the avoidance of or locating internal organs or passages of the body during surgery and more particularly to a method employing and to apparatus including an infrared emitting source and a detection system one or the other of which is inserted into the organ or passage and the other located adjacent the organ or body to thus indicate proximity thereto of an instrument inserted into the body and to which one of the source or the detector is adjacent to, thus assisting in locating or avoiding during surgery the organ or duct in which one of the members is inserted.

BACKGROUND OF THE INVENTION

During surgery on the human body, it is essential that organs or passages, such as the urethra and ureter, not be cut. The presence of blood, sponges, intervening tissue and the like make it extremely difficult to locate with great accuracy such organs or passages in the vicinity and particularly immediate vicinity of the region on which surgery is being performed.

Light emitting catheters are used to detect irregularities in a duct, vessel, organ or the like. U.S. Pat. No. 4,248,214 provides an illuminated urethral catheter to assist a surgeon in locating the junction of the bladder and the urethra to permit the proper performance of the Marshall-Marchetti-Kranz procedure. U.S. Pat. No. 4,782,819 is representative of many patents using catheters for illuminating organs for internal inspection.

The use of infrared sensors internally of the body to locate heat generating body tissue, such as cancers, is disclosed in several patents, for instance, U.S. Pat. No. 4,784,128. U.S. Pat. No. 4,821,731 uses a sound generating catheter to image internal features of the body.

None of the references cited disclose the concept of employing an infrared generating catheter and infrared detector for the purpose of defining the location of the passage, organ, etc. so as to permit a surgeon working in the region to have a clear knowledge of the location of the region to be avoided.

OBJECTS OF THE INVENTION

It is an object of the present invention to provide an infrared emitting catheter for insertion into a passage, duct, organ or the like during surgery and an infrared detection system so as to precisely locate such and warn the surgeon of dangerous approach thereto.

It is another object of the present invention to provide a method of precisely locating organs, passages, ducts and the like whereby a surgeon will not invade the body part so located.

It is still another object of the present invention to provide a catheter for insertion into a body passage or the like that gives off infrared emissions over an extended region of the passage or the organ or may be configured as a point source.

Still another object of the present invention is to provide infrared detection systems that provide readily detected signals or displays clearly indicating the location of an infrared source in the body of a being.

Still another object of the present invention is to provide an electronic switch system and control system to inhibit cauterization or lasing based on the location of an infrared emitting catheter relative to the proximity of the detection system which is fixed to the cauterization or lasing instrument.

It is yet another object of the present invention to provide an infrared light source and an infrared light guide connected to an infrared detector positioned such as to provide an indication of the location of one or more body members.

It is yet another object of the present invention to provide in conjunction with a system using infrared light to locate internal body members a source of light for illuminating the area of a region adjacent such body members and a display system associated with such source of light to display the organ on a monitor if desired.

BRIEF DESCRIPTION OF THE PRESENT INVENTION

The present invention is described as employed to precisely locate ureters in the necessity to locate or in consequence of the danger to these passages particularly during performance of a hysterectomy. The infrared emitting catheter and detection system of the present invention is not limited to such use, but this use is illustrative of the utility of the apparatus and method.

The infrared emitting catheter comprises a flexible, polymeric, preferably round light guide encased in a flexible essentially infrared transparent outer covering. The light guide may be constructed of glass or polymer with or without cladding. The outer surface of the light guide is abraded or otherwise rendered infrared transparent over an extended area of its length so that infrared is essentially circumferentially emitted over the entire length of the duct, passage, etc., in the present example, the ureter.

A reflector may be placed at the distal end of the infrared emitting light guide to reflect any light energy not initially scattered out the side thereby to increase the efficiency of radiation from the guide.

In reference to the abraded emitting light guide, in another embodiment multiple fibers of different lengths are employed, i.e., a fiber bundle consisting of very thin light guides. More specifically, multiple small diameter (25 to 50 microns) fibers are assembled, twined, then terminated at approximately 1 to 10 mm increments in the emitting region of the emitting catheter. In addition, the terminus of the each small fiber in the bundle is cut at an angle so as to direct infrared out of the emitting catheter.

Various different types of infrared detectors may be used, such as infrared photodetectors, endoscopes, cameras, audible devices, systems in which the sound intensity and frequency vary as a function of proximity to the infrared emitting catheter and thus the passage, etc. The infrared source may be pulsed or modulated so that the intensity of a blinking light on a monitor or the like can provide an indication of proximity.

Regardless of the type of infrared detector employed an important feature of the invention is that with the use of infrared, intervening blood tissue, sponges and the like do not mask the emission and thus the incidence of unfortunate errors are, if not eliminated, at least materially reduced.

In a preferred embodiment, an emitter control circuit controls the energy to the emitting catheter. A safety detector in one embodiment is placed superior to the iliac crest. The safety detector determines the integrity of the coupling between the infrared emitting catheter and its control circuit and/or the continuity of the infrared emitting light guide, and actually may be the detector used during surgery and just looks for infrared emission when the system is turned on. If an audible system is employed the energy supplied to the infrared emitting catheter is adjusted to provide tone amplitude desired by the surgeon. If the safety detector fails to detect infrared emissions a warning tone is emitted.

As indicated above to locate the ureter during a surgical procedure, the infrared detector is placed in the site of the operation and moved as the surgeon penetrates new regions. The tone amplitude and/or frequency provides the indications necessary to locate the ureter or ureters. In the preferred embodiment an infrared emitting catheter is inserted preferably in both ureters.

Rather than insert the infrared detector into the operation site a light guide coupled to the detector may be inserted into the site. A 600 μm or 1000 μm light guide may be employed and is coupled to the infrared detector through an optical coupler.

The infrared detecting light guide may be physically coupled to the instrument employed for cutting. If, for instance, a laparoscopic electrocautery instrument is employed the infrared detector system may be employed to prevent energization of the instrument if the cauterizing has approached to close to the ureter and the infrared detector system is deactivated when the instrument is energized since heat generated by the cauterization process might otherwise deactivate the instrument.

The position of the infrared source and the light guide of the detector may be reversed with the light guide inserted into the organ to be protected with the source directed at the organ. A visual light source video camera and monitor may be employed with the system to provide a visual display of the organ.

The term "light guide" as used herein is employed to indicate a single light pipe or a bundle of their light conducting fibers or a combination of both.

The above and other features, objects and advantages of the present invention, together with the best means contemplated by the inventor thereof for carrying out his invention will become more apparent from reading the following description of a preferred embodiment and perusing the associated drawings in which:

BRIEF DESCRIPTION OF THE DRAWINGS

FIG. 8 illustrates the use of a light reflector with the infrared light guide;

FIG. 9 illustrates the use of a light guide in the detection apparatus of the system;

FIG. 10 illustrates the physical coupling of a light guide to a electrocautery instrument and the circuitry for controlling the interrelationship between the detector and instrument;

FIG. 11 illustrates the detector control circuit of FIG. 9 in block diagram form;

FIG. 12 illustrates in transverse cross-section an example of a catheter with a urine drainage channel;

FIG. 17 is an illustration of the system of FIG. 13 in conjunction with a television system for displaying the ureter on a monitor screen.

DETAILED DESCRIPTION OF THE PRESENT INVENTION

Figure 1:
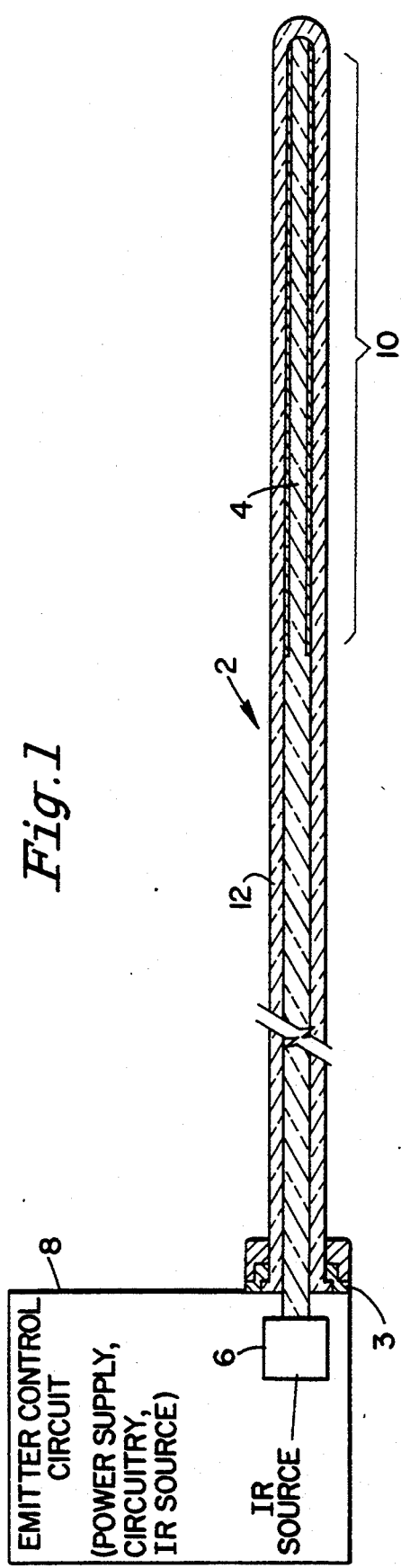
FIG. 1 is a view in longitudinal cross section of the catheter and light tube with controls.
Figure 2A:
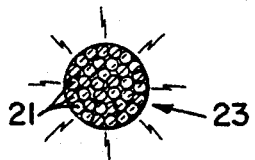
FIGS. 2A and 2B illustrate two different views of a catheter with multiple light guiding fibers of different lengths.
Figure 2B:

The term "light guide" refers to light emitting structures as illustrated in FIGS. 1 and 2.

Referring now specifically to FIG. 1 of the accompanying drawings, an emitting catheter 2 in accordance with the invention comprises an infrared emitting light guide 4 located inside of the emitting catheter and a source 6, of infrared energy driven by a variable voltage power supply 8 (D&B Power, Inc., Model F240-1000). Energy passes through an optical couple 3 (Motorola MFOE-1102) into the light guide, fabricated from either a polymeric or glass material (preferably fiber ESKA SH-4001 or SK-40) with or without cladding that passes infrared light with little attenuation. The light guide 4 has its surface abraded over a region 10 so the infrared may be circumferentially emitted in all directions into the surrounding region through the wall 12 of the catheter. The length of the region 10 is a function of the use to which the catheter is to be put; in the application being described, the length of the ureter about 30 cms. The overall length of the catheter is typically 65 cm and is 2.33 mm in diameter. The light guide is about 2 meters long.

In order to increase the efficiency of emission from the light guide 4, and reference is made to FIG. 8 of the accompanying drawings, an infrared reflector 5 reflects infrared not scattered from the region 10, reflecting it back into region 10 to provide additionally radiated infrared thus increasing the efficiency of the system.

Referring now to FIG. 2, the light emitting light guide may be fabricated from a plurality of light conducting fibers 21 of different lengths collected into a bundle 23. The ends 25 of the fibers are cut at an angle so that the light is projected out of the catheter at an angle to its length whereby to illuminate the surrounding area with infrared. The angle of the cut need not be uniform whereby to spread the infrared energy and insure substantially complete coverage of the surrounding region. The end of the fiber to be applied to a detector circuit is terminated with cable connector HFBR 450/HFBR 4511 from Hewlett Packard.

Figure 3:
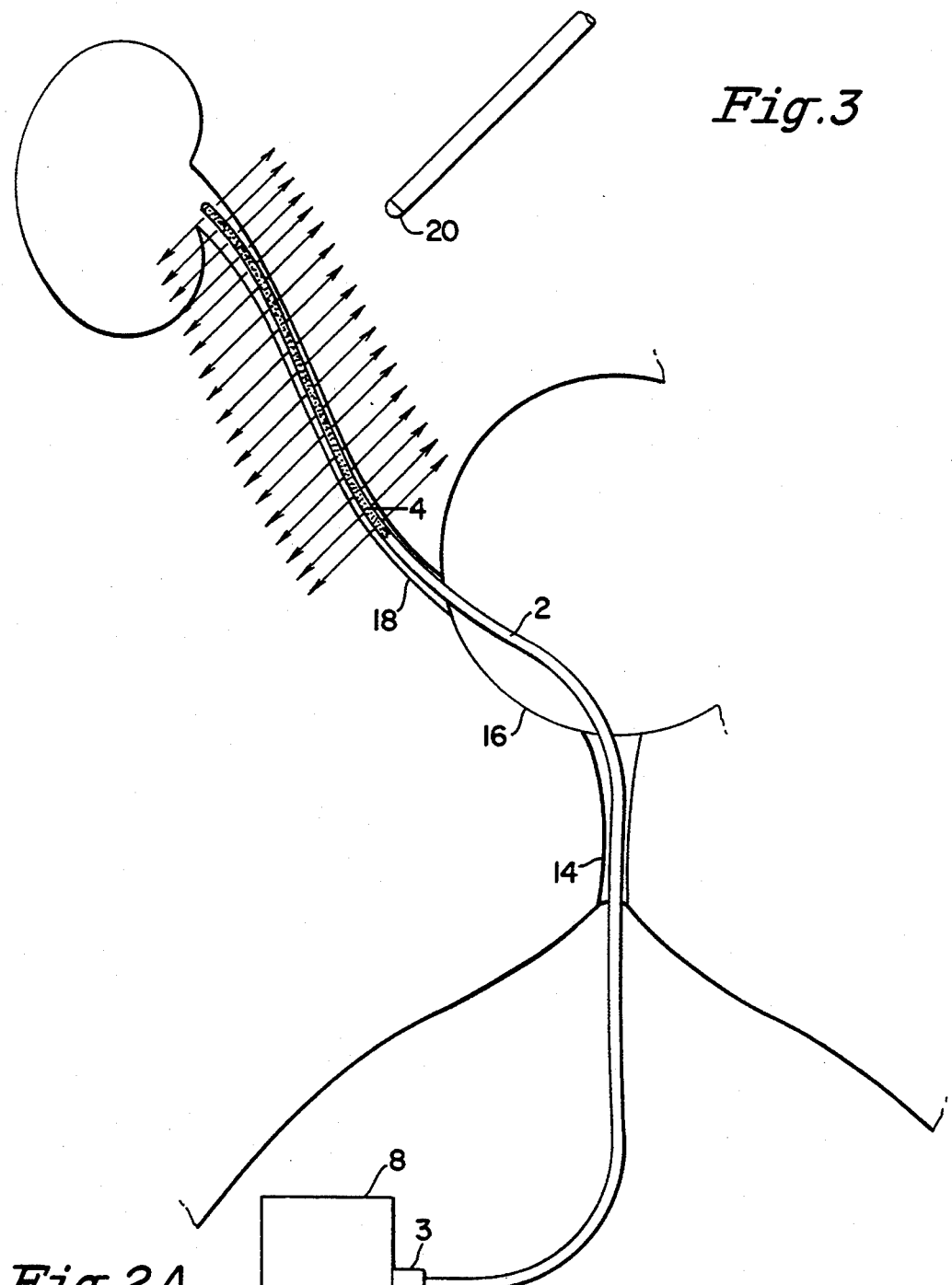
FIG. 3 illustrates in partial section the catheter inserted into the ureter.

Referring to FIG. 3 of the accompanying drawings, catheter 2 is inserted through the urethra 14 and the bladder 16 into the ureter 18 so as to emit infrared through the wall of the ureter into the surrounding region. An infrared detector 20 is used to sense the presence of the infrared energy radiated from the infrared emitting light guide 4. The energy transmitted to the fiber should not exceed 20 millivolts.

Figure 4:
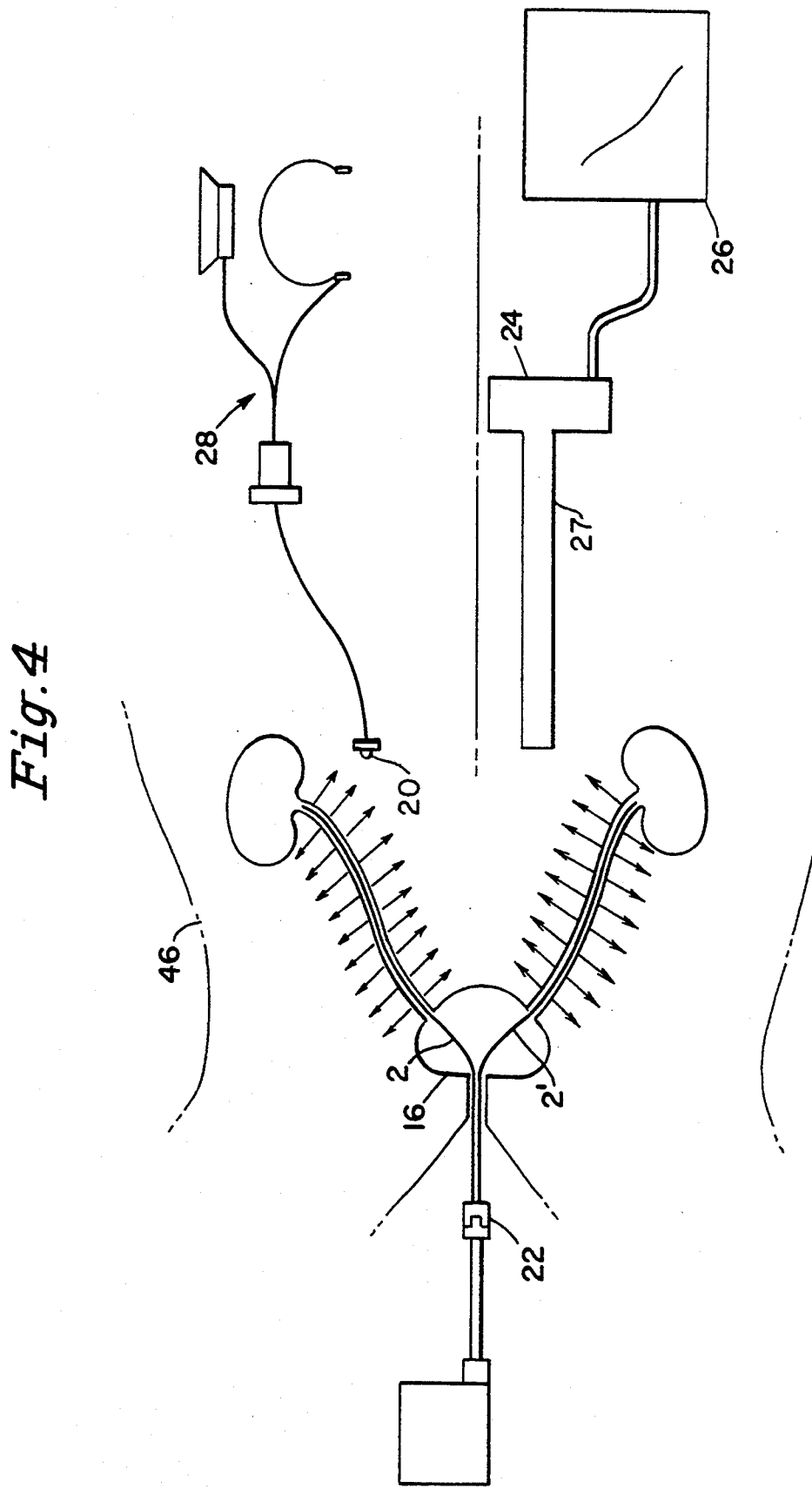
FIG. 4 illustrates catheters inserted into both ureters together with detection equipment.

Referring to FIG. 4 of the accompanying drawings, there is illustrated a modification of the system of FIG. 3 in which two catheters 2 and 2' are situated one in each ureter and driven from the same emitter control circuit 8 through a light splitter 22. Other than the use of two catheters and a light, splitter, the basic systems are the same. In FIG. 4, however, there is also illustrated the use of a small TV camera 24 fitted with a scope 27 to permit an image of the illuminated ureter to be displayed on a video monitor 26. The intensity of the image is a function of the proximity of the scope to the infrared source. Also as will become apparent in the subsequent discussion a beep resulting from modulation of the infrared may also be broadcast by the monitor as well as by an infrared detection system 28 employing the infrared detector 20.

A safety detector may be placed on the surface of the body near the location of the emitting catheter, superior to the iliac crest in the case of the ureters. The safety detector determines the integrity of the coupling between the infrared emitting catheter and its control circuit and/or the continuity of the infrared emitting light guide. An alarm sounds when infrared emissions are not sensed by the safety detector. An alarm sounds when infrared emissions are not sensed by the safety detector circuit which may be the same as the detector circuit of FIG. 4 of the accompanying drawings.

Figure 5:
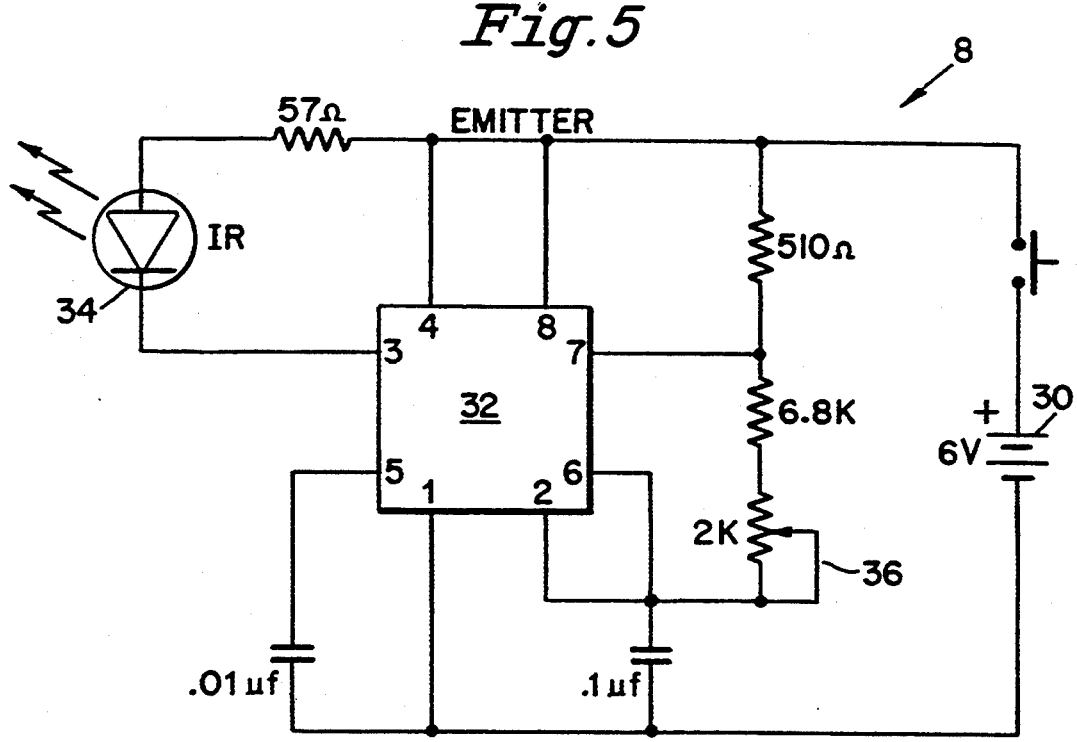
FIG. 5 is a block diagram of the control for light energy supplied to the light guide.

Referring now specifically to FIG. 5 of the accompanying drawings, there is illustrated in block diagram form the infrared transmitter employed with the present invention. The transmitter is purchasable from electronic supply stores and employs a 555 IC timer. A 6-volt battery 30 powers the timer 555 designated by reference numeral 32 which drives an infrared source or radiator 6 coupled to a light guide.

The timer 32 modulates the emitted signal at a frequency of approximately 800 Hz. The frequency is variable by a potentiometer or variable resistor 36 (2K ohms) connected between pins 2 and 7 of the element 32 in series with a 6.8K ohm resistor. The use of a modulated signal reduces response of the system to ambient or extraneous infrared energy and also provides a signal specific for the safety detector.

Figure 6:
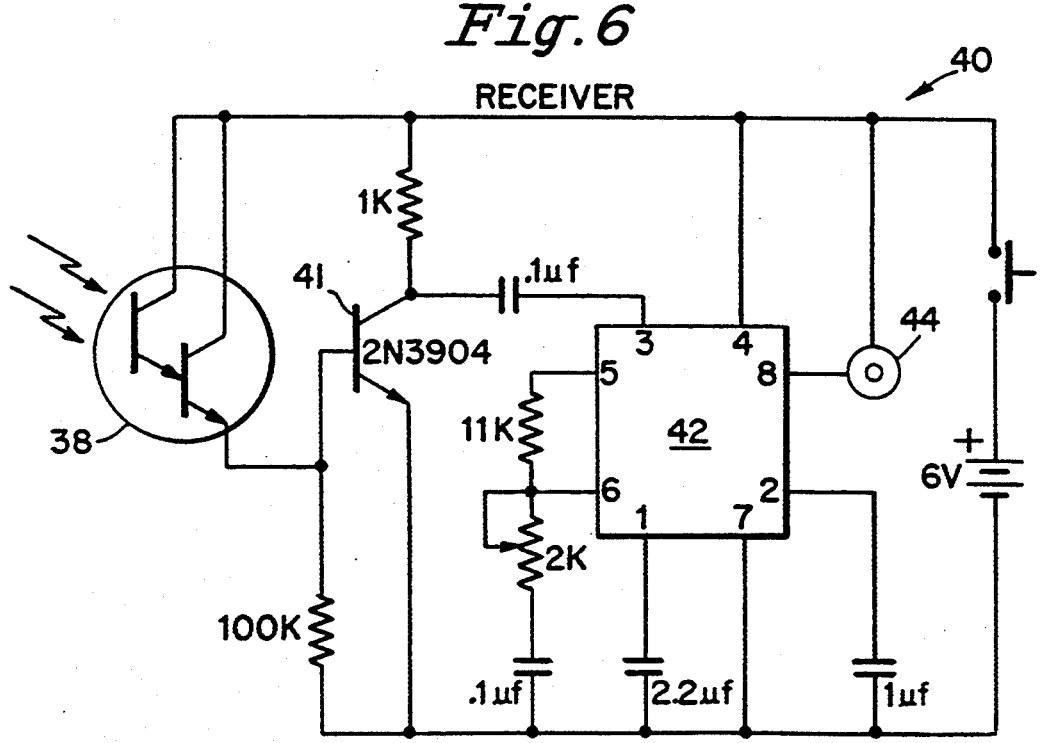
FIG. 6 is a circuit diagram of one form of infrared detector.

Infrared detector 38 and circuit 40 are illustrated in FIG. 6 of the accompanying drawings. The infrared detector is also available from electronic supply stores by the designation Motorola MFOD73 infrared receiver. The detector 38 drives a simple one transistor (2N3904) amplifier 41 supplying a signal to pin 3 of a 567 (IC) tone decoder 42. The tone decoder drives its output high and lights an LED or sounds a buzzer 44 whenever it detects a frequency within its band pass, in this example 800 Hz. With proper amplification the 567 IC 42 can drive a sound generator from its output at pin 8.

Figure 7:
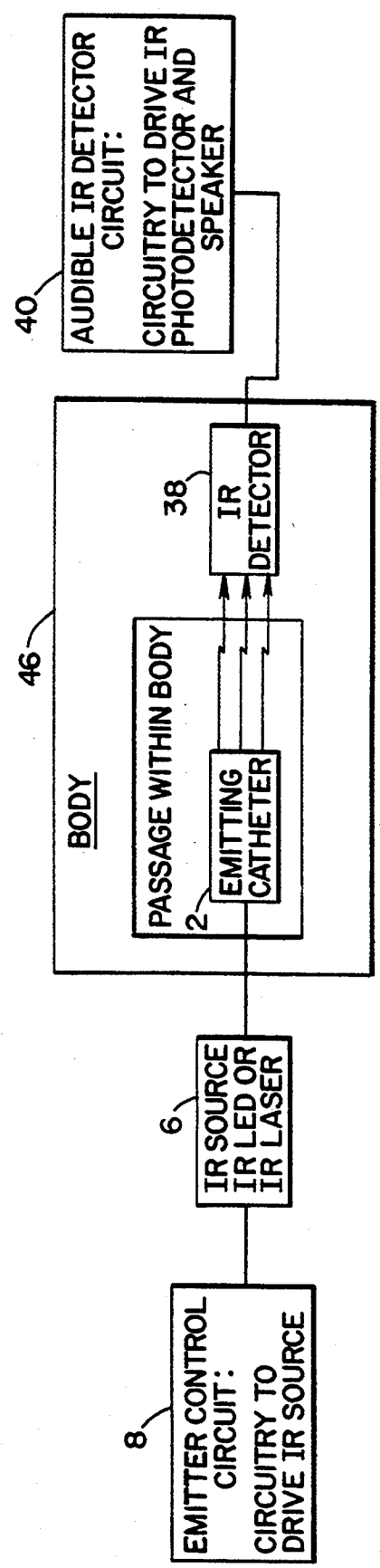
FIG. 7 is a block diagram of the system of the present invention.

A block diagram of the system of FIGS. 5 and 6 is illustrated in FIG. 7. Emitter control circuit 8 drives the infrared source 6 that supplies infrared to the emitting light guide 4 or light guides. The light guide(s) emits infrared into the body designated by the reference numeral 46, and is detected by detector 38. The detector 38 may be located in the body or if the scope 25-camera 24 arrangement is employed the camera 24 may be located externally of the body. The infrared detector may also be located on an instrument, endoscope or the like.

In FIG. 4 a scope 25 is inserted into the area of the operation to transmit the infrared to a camera 24 to display of information on a monitor. Similarly an infrared light guide may be employed to direct infrared energy from the interior of the area to an infrared detector external to the body. Referring to FIG. 9 of the accompanying drawings, an infrared light guide 50 may be equipped at its end remote from the ureter with an optical coupler 52 for coupling infrared energy to an infrared photodetector 54.

The guide 50 typically can transmit light in the infrared range, have a diameter of 1000 μm and is designed to be inserted into the body to direct infrared energy, the detector 54 external to the body.

The light guide of FIG. 9 may be employed in one example with a laparoscopic electrocautery instrument. Referring to FIG. 10 of the accompanying drawings, an electrocautery instrument 56 is energized from a source 58 via a detector control circuit 63 which receives a signal from detector 68 via light guide 59 to control excitation of the instrument.

Referring to FIG. 11, the details of the control 63 is illustrated, an infrared detector 68 is connected through an infrared photodetector circuit 70 to a voltage comparator 66 and a speaker transistor switch 64. The voltage comparator 66 compares the voltage from circuit 70 with a reference voltage and produces an output signal on lead 60 indicative of the level of voltage from circuit 64 relative to the level of the reference voltage. The lead 60 is connected to provide an input signal to the transistor switch 61 and also to an AND gate 72. The output of the AND gate 72 is applied through an inverter 75 to the speaker switch 64. The output signal from the speaker switch 64 is applied to a speaker-speaker circuit 74.

In operation, when the output voltage from the infrared photodetector circuit 70 equals or exceed the variable reference voltage in comparator 66, the current to the electrocautery transistor switch 61 goes to zero, thus opening the circuit between the electrocautery power supply 58 and the electrocautery instrument 56 and shutting the instrument off. Otherwise, as long as the output voltage from the infrared photodetector circuit is below the variable reference voltage at the comparator, the circuit between the electrocautery power supply and the electrocautery instrument remains closed.

Referring to the AND gate 72, when both inputs to the AND gate are high, indicating the use of the electrocautery instrument 56 and that voltage to the comparator from the infrared photodetector circuit is below the threshold voltage, the output of the AND gate goes high and the output of the inverter 75 goes low, driving the speaker transistor switch 64 off. Thus, the power to the speaker is suspended temporarily. Once cauterization is complete, power to the speaker and speaker circuit is restored and the detector may be employed to detect initial correct operation of the catheter.

It should be noted that the cauterization process may cause sufficient heat to shut off the instrument before it approaches dangerously close to the ureter. This problem is readily overcome by simply de-energizing the instrument in which case the speaker circuit is operational and will sound if approach to the ureter is too close for safety.

Referring now specifically to FIG. 12, a catheter 76 having a urine drainage channel is illustrated. The catheter includes a light emitting guide 78 and a drainage channel 80. Urine in the channel 80 reduces the infrared energy passing through the channel but once the catheter has entered the ureter, urine flow is in the form of occasional drops so that little attenuation of infrared energy occurs and even then it is sporadic.

Figure 13:
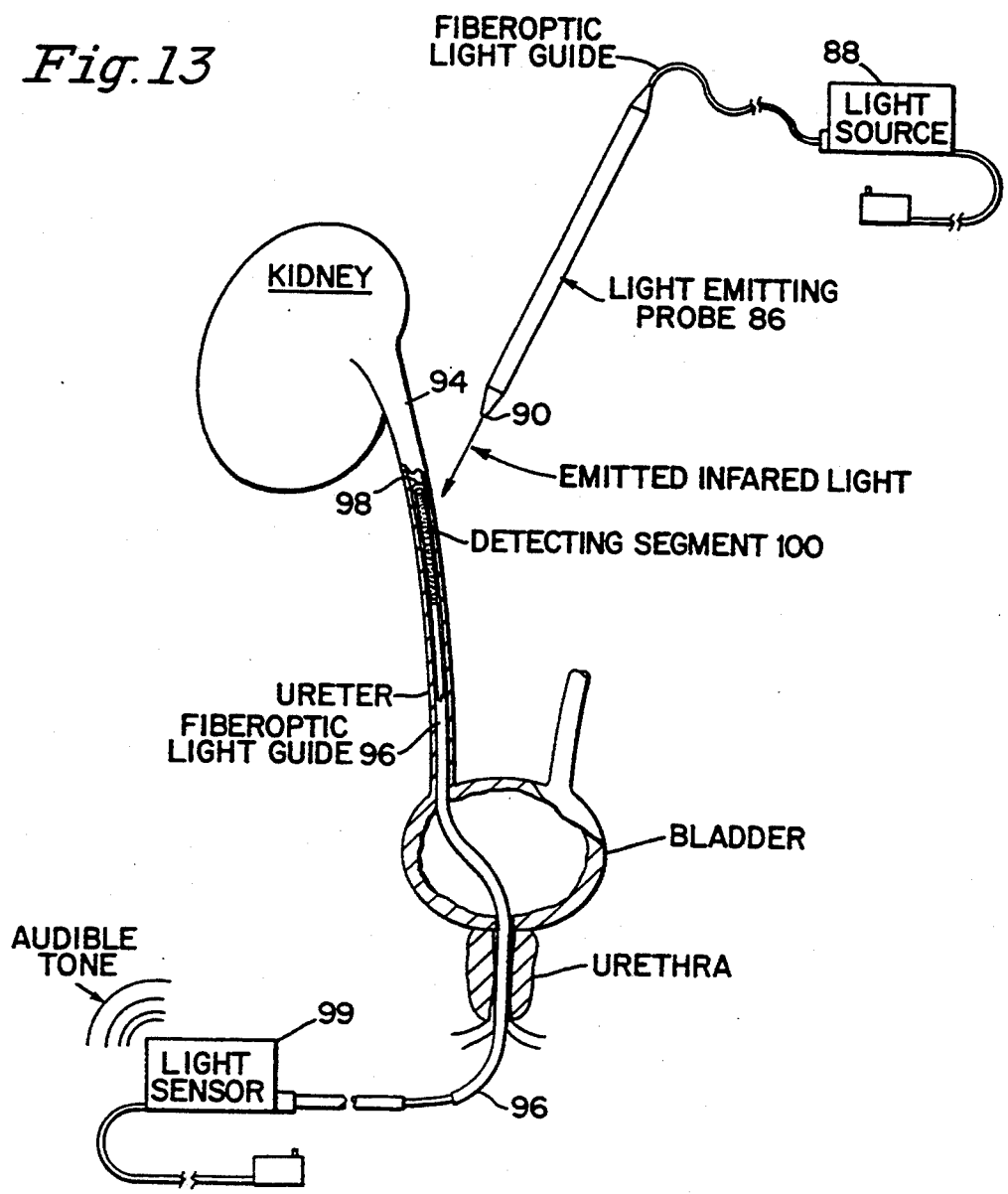
FIG. 13 is an illustration of an arrangement in which the locations of the probe and the guide are reversed relative to FIG. 3.

Referring now specifically to FIG. 13, there is illustrated a configuration in which the locations of the infrared light emitting body and the infrared detector have been reversed.

A light emitting probe 86 receives pulsed infrared energy from a light source 88 described subsequently. The end 90 of the probe 86 is manipulated until light sensor 99 emits an audible tone indicating thereby the location of ureter 94. More specifically, a fiber optic light guide 96 is located in a catheter 98 positioned in the ureter 94. The light guide is provided with a detecting segment 100, located over an extended longitudinal region of the guide 96 (20 cms) completely around the circumference of the guide.

The light guide directs infrared energy to a sensor 99 which, as indicated above, emits an audible tone when it receives energy of a magnitude that indicates the position of the probe end 90 relative to the organ, in this case, the ureter.

Figure 14:
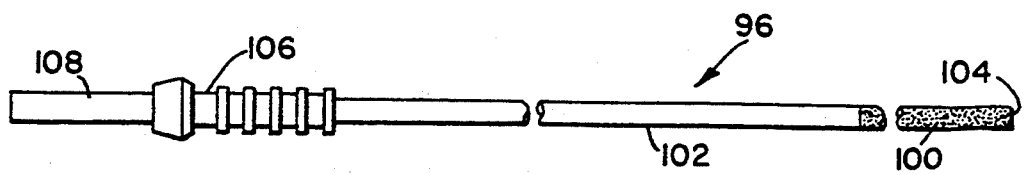
FIG. 14 is an illustration of light guide employed in the apparatus of FIG. 13.
Figure 16:
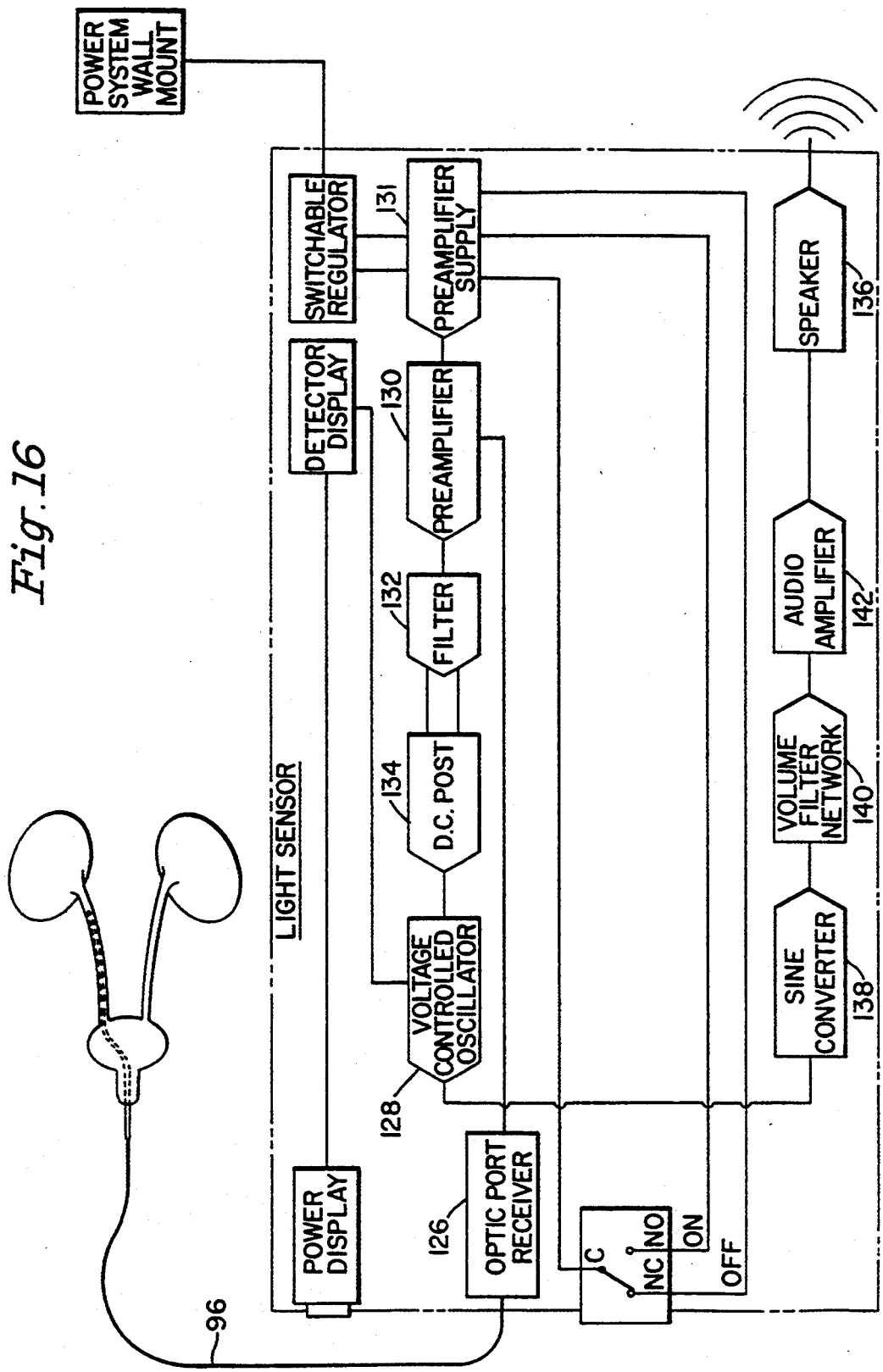
FIG. 16 is a block diagram of the electrical system associated with the light guide of the present invention.

Referring now to FIG. 14 of the accompanying drawings, the light guide comprises a fiber optical bundle 102 (see FIG. 2) having a distal end 104, with a roughened (abraded or scored) surface 100 (about 20 cm long) so that infrared light can penetrate into the bundle and be directed along the fibers through an optical connector 106 to a clear plastic rod 108 to an optic port receiver 126 (see FIG. 16) (Motorola MLED 73) in a detector circuit which may be included in the circuit of FIG. 16. In the preferred embodiment of the invention the guide 102 is Mitsuibishi light fiber ESKA SK40 and the connector 106 AMP's Optimatic Optical Connector 228087-1.

Figure 15:
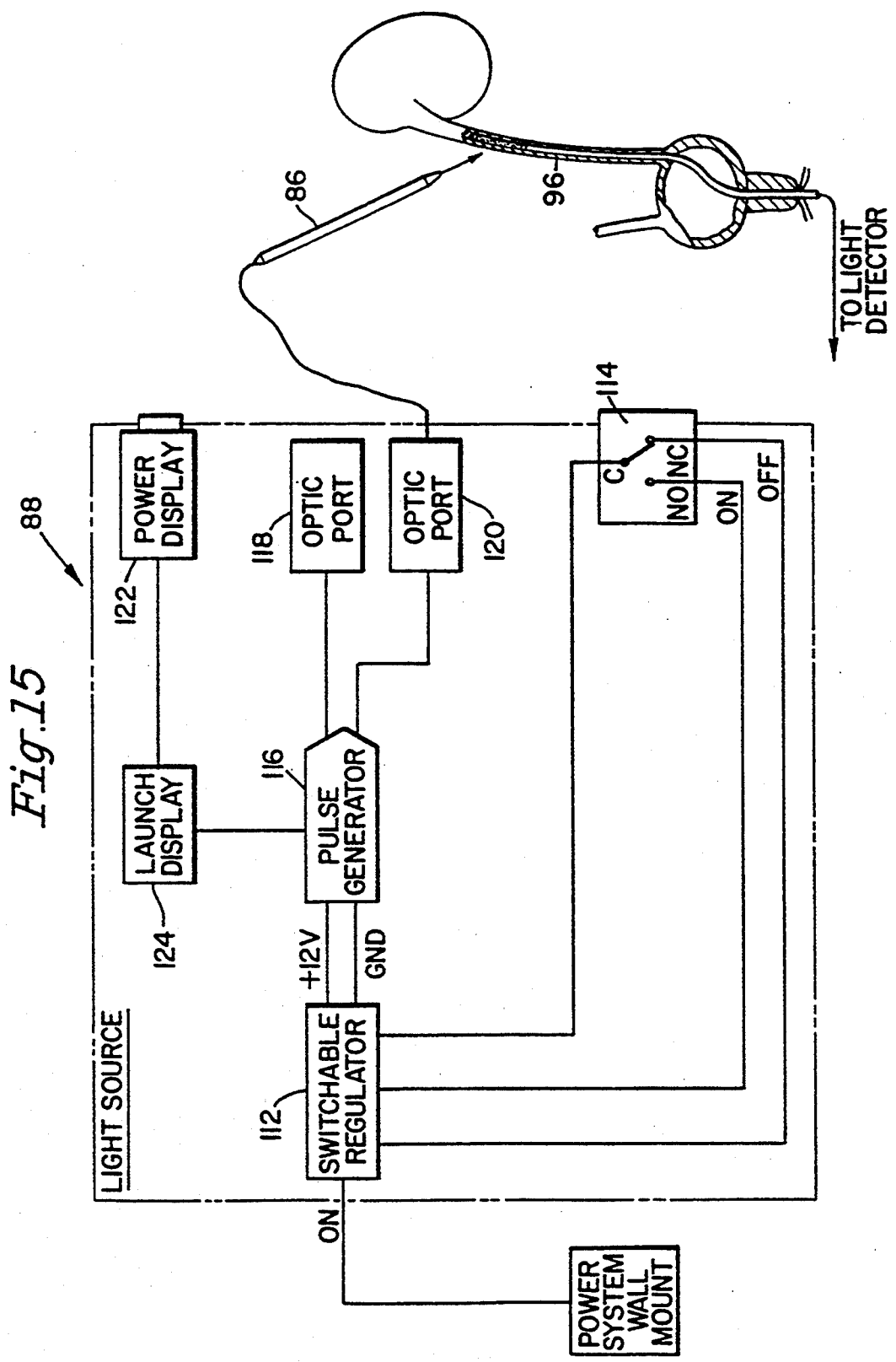
FIG. 15 is a block diagram of the electrical system associated with the probe illustrated in FIG. 13.

The light source 88 is illustrated in block diagram form in FIG. 15 of the accompanying drawings. Referring to FIG. 15 a regulator 112 driven by ac through on-off switch 114 provides regulated +12 volts to a pulse generator 116. The pulse generator produces triangular or sawtooth waves and drives a pair of optic ports 118 and 120, port 120 being illustrated as providing infrared energy to the light emitting probe 86 at about 5 millivolts. The optic port 120 converts pulsed electrical energy from generator 116 into pulsed infrared energy that is applied to the probe. The probe 86 is the same as light guide 96 except that no region is roughened and light is emitted only from the end of the probe 86. Complete galvanic isolation is thus provided. A segment type power display 122 is driven by a display driver 124 of conventional design. The display is a light emitting bar; the display having nine segments to indicate the level of the energy launched.

Referring now specifically to FIG. 16 of the accompanying drawings., light from the light detector guide 96 is fed to an optic port receiver 126 (see FIG. 16) that converts the light energy to electrical energy. Again, complete galvanic isolation is provided. The output of receiver 126 is passed to a voltage controlled oscillator 128 through a preamplifier 130, filter 132 dc post amplifier 134. A preamplifier 131 provides isolated low noise regulated voltage to the preamplifier 130. The output frequency of oscillator 128 is triangular wave and is a function of the level of the dc voltage output from amplifier 134 thus providing an indication of the amplitude of the light impinging upon the guide 96.

The output voltage of the oscillator 128 is fed to a speaker 136 serially through a sine converter 138, volume filter network 140 and audio amplifier. Thus the sound of the output of the speaker is a function of the proximity of the probe 86 to the ureter. Specifically, defining the exact function of each of the above elements the preamplifier 130 discriminates between the pulsed light received and background radiation received from the sources. It attenuates background light and amplifies the pulsed light signal. The filter 132 includes a peak average detector that splits the preamplified signal into peak and average components while the dc post amplifier 134, which is a high pass filter, accentuates the difference between the peak (high frequency) and average (low frequency) signal components. The voltage controlled oscillator 128 converts the difference between the peak and average components into a sawtooth voltage that is converted to a sine wave by the sine converter 138. The volume filter network permits control of the volume and also reduces the base tones.

It should also be noted that the difference signal is provided by the VCO to a detector display that drives a bar type indicator such as illustrated in FIG. 13.

Referring now specifically to FIG. 17 of the accompanying drawings, there is illustrated the system of FIG. 13 in conjunction with an illumination apparatus comprising a laparoscopic light source 150 providing light energy to a light conductor 152. The light conductor illuminates a surgical field with light from source 150 having no infrared component. Light from the area of the operation is also transmitted through the light conductor 152 to a laparoscopic camera 154 with the infrared blocking filter removed from the chip or chips in a three chip camera. The camera 154 transmits a signal over lead 156 to a monitor 158 which provides a display of the ureter in this case.

It is apparent that other sources of infrared are ambient in the body but the use of a pulsed infrared source to the light guide eliminates signals from such sources.

Penetration into the body for both the probe 86 and light guide 152 is through conventional trocars. The probe 86 is secured by conventional techniques to the instruments inserted into the body for surgical procedures.

There are occasions, for instance in brain surgery on tumors, when a point source is indicated. In such instances the probe emits infrared light only from its end and acts as an indicator of the tumor's location.

Once given the above disclosure, many other features, modifications and improvements will become apparent to the skilled artisan. Such other modifications, features and improvements are, therefore, considered a part of this invention, the scope of which is to be determined by the following claims.

What is claimed is:

1. The method of locating or reducing the danger during surgery or other invasion of a body of injury to body members into which a catheter may be inserted comprising the steps of inserting a catheter into the body member, inserting an elongated infrared light guide having a region that emits such light into the catheter, directing infrared light energy into the light guide, indicating the proximity of an ongoing surgical procedure to the body member by determining the intensity of the infrared radiation exiting the body member at the surgical site.

2. The method according to claim 1 further including the step of inserting an infrared detector into a surgical opening in the vicinity of the body member.

3. The method according to claim 1 further including the step of energizing an infrared detector located external to a body undergoing a surgical procedure, and directing infrared energy emitted from the body member to the infrared detector located external to the body.

4. The method according to claim 1 including the step of modulating the light at a detectable frequency and producing a signal indicative of the modulating frequency.

5. The method according to claim 1 reflecting from a distal end of the light guide infrared energy not emitted from the light guide.

6. The method according to claim 1 energizing an infrared detector located external to the body undergoing a surgical procedure, and employing a light guide insertable into the body for directing infrared energy to the detector.

7. The method according to claim 6, physically attaching the last mentioned light guide to an energizable surgical instrument, and employing an infrared responsive circuit for disabling the surgical instrument in response to a level of detected infrared energy above a predetermined level.

8. The method according to claim 7, disabling the infrared responsive circuit during energization of the surgical instrument.

9. Apparatus for detecting the proximity to at least one body member adjacent an anatomical body on which a surgical procedure is being conducted comprising a catheter for insertion into a body member, a light guide having means to emit light transverse to its length along a length thereof inserted into said catheter, a source of infrared light energy located to direct infrared light energy into said light guide, an infrared light energy detector located such as to detect infrared light energy emitted by said light guide, and means responsive to the intensity of the infrared light energy detected by said detector for producing a signal of an intensity indicative of the proximity of the surgical procedure to the body member, a signal generating device, means for applying said signal to said signal generating device, said signal generating device having means for producing an indication of the intensity of said signal.

10. The apparatus according to claim 9 wherein said infrared detector configured to be insertable into the body at the surgical sight.

11. The apparatus according to claim 10 wherein said source of infrared light energy has means for producing a modulated signal of a predetermined frequency.

12. The apparatus according to claim 11 wherein said signal generating device includes means for responding only to modulation of the predetermined frequency.

13. The apparatus according to claim 12 wherein said means for producing an indication of the intensity of said signal includes means providing a signal detectable by human senses that is a function of the intensity of the signal produced by the signal generating device.

14. The apparatus according to claim 12 wherein said source of infrared light energy includes means for producing a modulated signal at approximately 800 Hz.

15. The apparatus according to claim 9 wherein said infrared detector is adapted to be located external to the body, and means for directing to the infrared detector infrared light energy of an intensity that is a function of the proximity of said means to the body member.

16. An apparatus according to claim 9 further comprising an infrared reflector at an end of said light guide remote from said source whereby to reflect infrared light energy not emitted back into the emitting region.

17. An apparatus according to claim 9 wherein said infrared detector is adapted to be located external to the body and further comprising a further light guide insertable into a site of an operation for transmitting infrared light energy from a region internal to the body to said infrared detector.

18. An apparatus according to claim 17 wherein said further light guide is configured to be connected to an energizable surgical instrument, and further comprising a control circuit, said control circuit connected to receive infrared light energy from said further light guide, said control circuit responsive to said infrared light energy for preventing energization of the surgical instrument to which said further light guide is to be connected when infrared light energy supplied to said infrared light detector is above a predetermined level and for de-energizing the infrared detector when such surgical instrument is energized.

19. An apparatus according to claim 9 wherein said light guide comprises a plurality of thin light conducting fibers of different lengths, said fibers terminating in angled facets whereby to direct infrared light energy out of said catheter.

20. An apparatus according to claim 19 wherein said fibers have ends lying at 1 mm to 10 mm intervals adjacent an end of the catheter.

21. The method of determining during surgery or other intentional invasion of the body, the proximity of an instrument to a body member other than the body member on which a procedure is to be conducted, comprising the steps of inserting into the body a source of infrared light energy, inserting into the body an infrared light guide, inserting one of said source and guide into said body member other than the body member on which a procedure is to be performed, establishing the position of the other of the source and guide as a function of the position of the instrument relative to the latter body member, and indicating the proximity of the other of said guide and source relative to said latter body member.

22. The method according to claim 21,
physically attaching the source to an instrument to be inserted into the body for procedural purposes.

23. The method according to claim 21,
pulsing the source to provide a signal that may be differentiated from background infrared energy.

24. The method according to claim 23,
illuminating the area of entry into the body external to the organ into which one of the source and guide has been inserted, and
monitoring such area with an infrared sensitive video camera and monitor.

25. Apparatus for detecting the proximity of an instrument to at least one body member adjacent an anatomical body on which a procedure is to be performed comprising
a source of infrared energy,
an infrared detector,
a light guide connected to said infrared detector for guiding infrared energy impinging thereon to said infrared detector,
one of said source and light guide adapted to be inserted into the body member proximate the anatomical body,
the other of said source and light guide positioned relative to the said one of said source and light guide such that infrared energy from said source impinges upon said light guide, and
means for producing a signal displaying the proximity of an instrument to the body member.

26. The apparatus according to claim 25 further comprising means for pulsing said source.

27. The apparatus according to claim 26 wherein said means for producing a signal includes,
means for producing a signal determined by the difference between the peak of said pulsed light and background infrared, and
means for producing a voltage of a frequency determined by the amplitude of said signal.

28. The apparatus according to claim 27 further comprising
means connected to receive said voltage for converting said last-mentioned voltage to a sine wave and
a generator connected to said means for connecting the sine wave signal to produce an audible signal.

29. Apparatus for detecting the proximity of an instrument to at least one body member adjacent an anatomical body on which a procedure is being conducted comprising
a light guide having means to emit light transverse to its length along a length thereof adapted to be inserted into a body member to be protected during procedures being conducted on the anatomical body by an instrument adjacent to the body member,
a light source having infrared energy located to direct light energy into said light guide,
an infrared detector located such as to detect infrared energy emitted by said light guide, and
a signal generator having circuitry circuit means responsive to the intensity of the light energy detected by said detector for producing a signal indicative of the proximity of the procedure to the body member.

* * * * *